United States Patent [19]

Naito

[11] 4,235,245
[45] Nov. 25, 1980

[54] DEVICE FOR PICKING UP TISSUES FROM A BODY CAVITY

[75] Inventor: Masayoshi Naito, Hachioji, Japan

[73] Assignee: Olympus Optical Co., Ltd., Tokyo, Japan

[21] Appl. No.: 958,622

[22] Filed: Nov. 8, 1978

[30] Foreign Application Priority Data

Nov. 8, 1977 [JP] Japan .......................... 52-149795[U]

[51] Int. Cl.³ .............................................. A61B 10/00
[52] U.S. Cl. ..................................................... 128/756
[58] Field of Search .............. 128/772, 754, 756, 757, 128/759, 749, 751; 74/501 R

[56] References Cited

U.S. PATENT DOCUMENTS

| | | | |
|---|---|---|---|
| 2,955,592 | 10/1960 | MacLean | 128/756 |
| 3,407,684 | 10/1968 | Van Noord | 74/501 R |
| 3,452,740 | 7/1969 | Muller | 128/DIG. 9 |
| 3,552,384 | 1/1971 | Pierie et al. | 128/DIG. 9 |
| 3,613,664 | 10/1971 | Willson et al. | 128/756 |
| 3,808,908 | 5/1974 | Guerr | 74/501 R |
| 3,960,032 | 6/1976 | Schiff | 74/501 R |
| 3,995,619 | 12/1976 | Glatzer | 128/749 X |

FOREIGN PATENT DOCUMENTS

2735706  2/1978  Fed. Rep. of Germany ........... 128/749

*Primary Examiner*—Kyle L. Howell

[57] ABSTRACT

A device for picking up tissues comprises a flexible outer sheath, an extension wire extending through the outer sheath, a connector fixed by one end of the wire and having an outer diameter larger than the inner diameter of the outer sheath for abutting on one end of the outer sheath, a tissue picking-up section connected to said one end of the wire by the connector, a wire holding section for holding the other end of the extension wire and receiving the other end of the outer sheath, a chamber formed in the wire holding section, and a compression spring disposed in the wire holding section for resiliently urging the other end of the outer sheath toward the tissue picking-up section. The device is inserted into an endoscope disposed in a body cavity, and its outer sheath can be easily bent according to the shape of the body cavity.

6 Claims, 8 Drawing Figures

PRIOR ART

DEVICE FOR PICKING UP TISSUES FROM A BODY CAVITY

BACKGROUND OF THE INVENTION

This invention relates to a device for picking up tissues from a body cavity, which is used in combination with an endoscope.

As shown in FIG. 1, a known tissue picking-up device comprises an outer sheath 1 constituted by a coiled metal wire element, an extension wire 2 extending through the outer sheath 1, a tissue picking-up section 4 connected to one end of the wire 2 by a connector 5, and a holding section 6 for holding the other end of the wire 2. To pick up desired tissues or cells from a body cavity it is necessary to move the tissue picking-up section 4 for a small distance. Since the section 4 is moved by moving the outer sheath 1, a relative movement must not occur between the sheath 1 and the section 4. To avoid such a relative movement, the wire 2 is strongly pulled toward the holding section 6 and held by the holding section 6 so that the connector 5 always abuts on the distal end of the outer sheath 1.

Let it be assumed that the metal wire constituting the outer sheath 1 and the extension wire 2 be each made of a rigid body but can be flexed. When the outer sheath 1 is bent as shown in FIG. 2, that portion of the outer sheath 1 which is adjacent to its center of curvature does not substantially shrink lengthwise thereof. But, since the extension wire 2 is connected to the holding section 6 and the connector 5 abutting against the distal end of the outer sheath 1, the wire 2 must be elongated, depending on how much the outer sheath 1 is bent.

In practice, some clearance is provided between the adjacent turns of the coil constituting the sheath 1. The turns can be elastically deformed to some extent, and the wire 2 can be elastically elongated to some degree due to the fact that the coiled metal wire element and the extension wire are not completely rigid bodies. The outer sheath 1 can, therefore, be bent but to a limited extent. When the sheath 1 is bent beyond the limited extent, however, the wire 2 would be cut or be broken at the connector 5 or slip off the holding section 6.

While it is inserted into a meandering body cavity, an endoscope is often bent very much and so is its forceps channel. There is a reverse possibility that the known device as illustrated in FIG. 1 cannot be inserted into the forceps channel which is bent too much. Moreover, if the outer sheath 1 is bent and the wire 2 is cut in a body cavity, a part of the cut wire 2, the tissue picking-up section 4 and the connector 5 may fall into the body cavity from the endoscope and adversely remain in the body cavity.

SUMMARY OF THE INVENTION

An object of this invention is to provide a device for picking up tissues the outer sheath of which can be bent sufficiently without damaging any other constituent members of the device especially without breaking an extension wire and which can therefore be used in combination with an endoscope.

A device for picking up tissues according to this invention comprises a flexible outer sheath, an extension wire extending through the outer sheath, a connector fixed to one end of the wire and having an outer diameter larger than the inner diameter of the outer sheath for abutting on one corresponding end of the outer sheath, a tissue picking-up section connected to said one end of the wire by the connector, a wire holding section for holding the other end of the wire and receiving the other end of the outer sheath, and resilient means provided in the holding section for urging the other end of the outer sheath toward the tissue picking-up section.

As the outer sheath is bent, the resilient means allows the extension wire to be moved toward the tissue picking-up section depending on the curvature of the outer sheath whereby the outer sheath is easily bent much without damaging any other parts of the device.

DETAILED DESCRIPTION OF THE PREFERRED EMBODIMENTS

Figure 1:
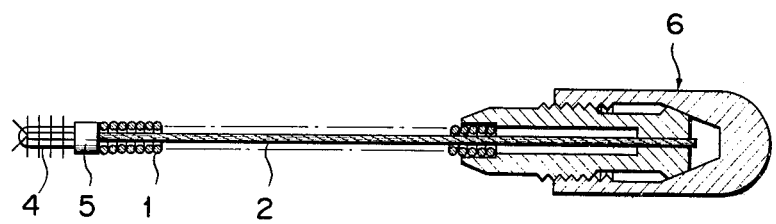
FIG. 1 is a longitudinal sectional view of a known device for picking up tissues.
Figure 2:
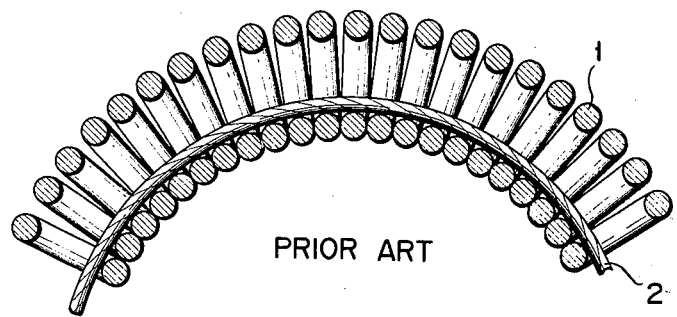
FIG. 2 is a longitudinal sectional view of the outer sheath and wire of the known device of FIG. 1, when the outer sheath is bent.
Figure 3:
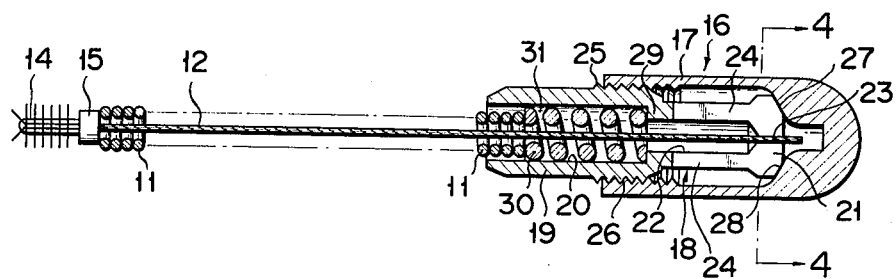
FIG. 3 is a longitudinal sectional view of an embodiment of the device for picking up tissues according to this invention.

As shown in FIG. 3, a device for picking up tissues according to this invention has an outer sheath 11 comprising a coiled metal wire element or the like and a metallic extension wire 12 extending through the outer sheath 11. One end of the extension wire 12 is connected to a tissue picking-up section 14 including a hard nylon brush, for example, by means of a hollow cylindrical connector 15. The connector 15 has an outer diameter which is larger than the inner diameter of the outer sheath 11. The connector 15, therefore, abuts on the distal end of the outer sheath 11, thereby preventing the tissue picking-up section 14 from being pulled into the outer sheath 11.

The device shown in FIG. 3 further includes a wire holding section 16 which comprises an outer tubular member 17 and a chucking member 18. The chucking member 18 comprises a sleeve 19 and a chuck 21 which are integrally formed with each other. The sleeve 19 has a large axial hole 20. The chuck 21 has an axial hole 22 smaller than the hole 20 and another axial hole 23 a little larger than the diameter of the wire 12. The chuck 21 has a plurality of axial slits 24 which passes the axis of the chuck 21. These slits 24 split the chuck 21 into a plurality of parts (four parts in FIG. 4).

Said other end of the wire 12 is inserted into the axial hole 20, then the axial hole 22 and finally the axial hole 23. The sleeve 19 has an external screw 25 on its outer periphery, and the tubular member 17 has an internal screw 26 on its inner lateral wall. As the sleeve 19 is screwed into the tubular member 17, a conical surface 27 on the top portion of the chuck 21 is gradually pressed into a substantially conical concave 28 formed in the outer tubular member 17. As the conical surface 27 is pushed into the concave 28, the chuck 21 gradually closes thereby to hold said other end of the wire 12 steadfastly.

That one end of the outer sheath 11 which is remote from the connector 15 is inserted into the axial hole 20 of the sleeve 19. In the axial hole 20 of the sleeve 19, a compression spring 30 is disposed between said one end of the outer sheath 11 and a shoulder 29 defined by the sleeve 19 and the chuck 21. The spring 30 always resiliently urges the outer sheath 11 toward the connector 15, whereby the connector 15 always abuts on said one end of the outer sheath 11.

As the device is inserted into a forceps channel of an endoscope inserted into a body cavity, the outer sheath 11 is bent according to the radius of curvature of the forceps channel. The length of the portion of the wire 12 between the free end of the sleeve 19 and the connector 15 does not change, however largely the outer sheath 11 is bent. As the sheath 11 is bent, said one end of the sheath 11 is forced deeper into the sleeve 19 against the resilient force of the compression spring 30. Thus, if a proper spring force is selected for the spring 30, the outer sheath 11 can be bent to a large extent without varying so much the force applied on the wire 12 and the connector 15. In other words, even if the outer sheath 11 is bent very much, no excessive force would be exerted on the wire 12 or the connector 15. The wire 12 is neither cut at its intermediate portion nor broken at the connector 15. Also, the wire 12 does not slip off the wire holding section 16. The tissue picking-up section 14 does not fall in the body cavity, and thus it is not left therein. In addition, the device shown in FIG. 3 picks up desired tissues from the body cavity without fail.

The axial hole 20 of the sleeve 19 comprises a chamber 31 for housing the compression spring 30.

Figure 5:
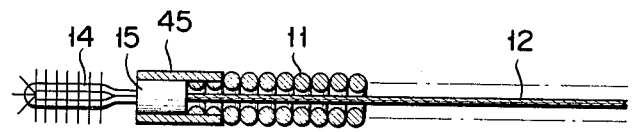
FIG. 5 is a longitudinal sectional view of the main part of another device according to this invention.

As shown in FIG. 5 of another embodiment, one end of the outer sheath 11 which is connected to a tissue picking-up section 14 is inserted into a hollow cylindrical member 45 which surrounds the connector 15. The cylindrical member 45 prevents an extension wire 12 to be bent at its connecting portion with the connector 15.

Figure 6:
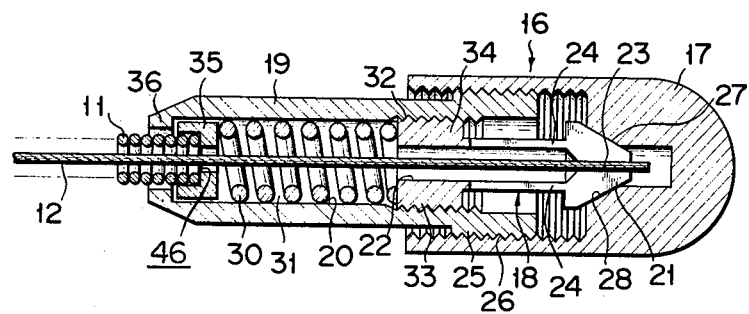
FIGS. 6 to 8 are respectively longitudinal sectional view of further embodiments of this invention.

FIG. 6 shows a wire holding section 16 which differs from the section 16 of the device illustrated in FIG. 3 in that a sleeve 19 and a chuck 21 are separate members. The sleeve 19 has an external screw 25 on its outer periphery and an internal screw 32 on its inner lateral wall, and is screwed into an outer tubular member 17 which has an internal screw 26 on its inner wall. A chucking member 18 has a thicker portion or barrel 34 which has an external thread 33 on its outer periphery. The thicker portion 34 makes a screw engagement with the sleeve 19 such that the degree of its insertion into the sleeve 19 can be adjusted by its turning. Thus, the force of the compression spring 30 can be adjusted by turning the thicker portion 34 of the chucking member 18.

In a chamber 31 defined in a sleeve 19, a compression spring 30 is disposed between the thicker portion 34 and a seat 35 having a U-shaped cross section. The sleeve 19 is provided at its free end with an inward extending flange 36 which prevents the seat 35 from slipping off the sleeve 19. The seat 35 receives one end of the outer sheath 11 so as to prevent the sheath 11 from being forced into the compression spring 30. The seat 35 has a central hole 46 through which an extension wire 12 extends.

Figure 7:
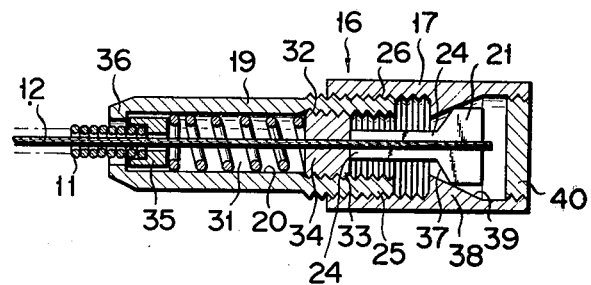

FIG. 7 shows another wire holding section 16. This wire holding section 16 is identical with the wire holding section 16 of FIG. 6 except that a chuck 21 has a conical rear surface portion 37 and that the inner wall 38 of a tubular member 17 is inclined to form a reversely conical concave or cavity 39. As the tubular member 17 is turned so as to be unscrewed from a sleeve 19, the conical rear surface portion 37 moves deeper into the concave 39, whereby the chuck 21 closes gradually to hold an extension wire 12 steadfastly. The conical concave 39 is covered by a lid 40 such that foreign matter does not enter the concave 39.

Figure 8:
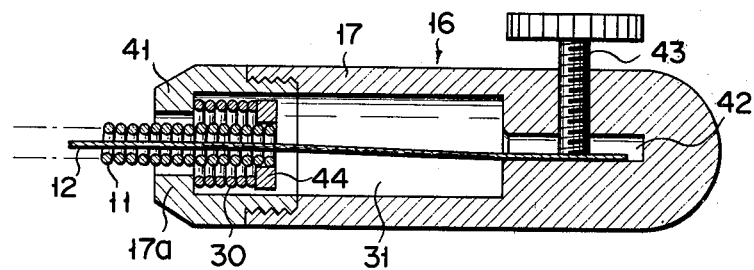

FIG. 8 shows a further wire holding section 16. An outer tubular member 17 closed at its proximal end portion has a chamber 31 extending therethrough from an inwardly extending flange 41 formed at its distal end to its intermediate portion. Further, it has a small axial hole 42 which extends through its proximal end portion and which has an inner diameter larger than the outer diameter of an extension wire 12. A set screw 43 is screwed in the lateral wall of the proximal end portion of the member 17, thereby to press the wire 12 firmly against the inner surface of the small axial hole 42. A seat 44 is disposed in the chamber 31. Through the seat 44 the wire 12 extends. To the seat 44 the proximal end of an outer sheath 11 is secured. A tension spring 30 is disposed between the flange 41 and the seat 44 and always resiliently urges the outer sheath 11 toward a connector 15 fixed to the distal end of the wire 12.

Figure 4:
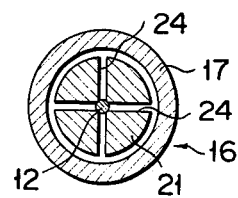
FIG. 4 is a cross sectional view of the device shown in FIG. 3, taken along line 4—4.

The embodiments of FIGS. 5 to 8 are operated in the same manner as the embodiment of FIGS. 3 and 4.

What is claimed is:

1. A device for picking up tissues from a body cavity comprising;
   a flexible outer sheath comprising a coiled wire element having two ends;
   an extension wire extending through said outer sheath and having two ends;
   a connector fixed at one of said two ends of said extension wire and having an outer diameter larger than the inner diameter of said outer sheath for abutting on one of said two ends of said outer sheath;
   a tissue picking-up section connected to one of said two ends of said extension wire by said connector;
   a wire holding section for holding the other end of said extension wire and receiving the other end of said outer sheath;
   a chamber formed in said wire holding section and allowing said extension wire to extend through said chamber; resilient urging means provided in said chamber and contacting said other end of said outer sheath for resiliently urging said other end of said outer sheath toward said tissue picking-up section; and
   said other end of said outer sheath being pulled into said chamber against said resilient urging means to prevent said extension wire from being applied with sufficient force to break said extension wire, as said outer sheath is bent.

2. The device according to claim 1, wherein said resiliently urging means comprises a compression spring.

3. The device according to claim 2, wherein said compression spring is engaged with the other end of said outer sheath with a seat interposed therebetween.

4. The device according to any one of claims 1 to 3, wherein said chamber is formed in a chucking member inserted into an outer tubular member which said wire holding section comprises.

5. The device according to claim 4, wherein said tubular member has a sleeve in which said chamber is formed.

6. The device according to any one of claims 1 to 3, wherein said wire holding section comprises a tubular member in which said chamber is formed.

* * * * *